United States Patent [19]

Malinow

[11] Patent Number: 4,602,005

[45] Date of Patent: * Jul. 22, 1986

[54] TIGOGENIN CELLOBIOSIDE FOR TREATING HYPERCHOLESTEROLEMIA AND ATHEROSCLEROSIS

[75] Inventor: M. Rene Malinow, Portland, Oreg.

[73] Assignee: Medical Research Foundation of Oregon, Beaverton, Oreg.

[*] Notice: The portion of the term of this patent subsequent to Jul. 22, 2003 has been disclaimed.

[21] Appl. No.: 602,298

[22] Filed: Apr. 20, 1984

Related U.S. Application Data

[63] Continuation-in-part of Ser. No. 379,098, May 17, 1982.

[51] Int. Cl.$^4$ .................... A01N 45/00; A61K 31/705
[52] U.S. Cl. .................................................... 514/26
[58] Field of Search .................. 260/239.55 A, 397.2; 563/6, 6.1; 424/182; 514/26

[56] References Cited

U.S. PATENT DOCUMENTS 4,260,603 4/1981 Pegel et al. ............................. 536/5

FOREIGN PATENT DOCUMENTS 7836823 12/1978 France .................................... 536/5

OTHER PUBLICATIONS

Kintya et al, "Search for Hypocholesteremic Agents Among a Group of Steroid Glycosides", Kim.-Farm, Zh. (Sep. 1981) 15:9, pp. 56–60 (Russian, Eng. trans. enclosed).
Lasur'evskii, et al., "Steroid Glycosidases from *Asparagus officinais* L.,-Doklady ANSSR (reports of the USSR Academy of Sciences), (1976), vol. 1, No. 6, pp. 1479–1481.
Perepelitsa et al., "A Chemical Study of the Steroid Glycosides of Tribulus Terrestris-IV. Steoid Saponins", Khimiya Priorodnykh Soedinenii, 260–261 (1975).
Schelocochkova et al, "Diosgenin and Neotigogenin Gluocosides", Khimiya Priorodnykh Soedinenii, 1:103–104 (1979).
Lazur'evskii et al, "Structure of Steroid Glycosides of Leaves of *Funkia ovata* Spr.", Doklady Akadamii Nauk SSSR, vol. 230, pp. 476–477 (1976).
Lazur'evskii et al, "Steroid Glycosides from Leaves of *Agava americana* L." Doklady Akademie Nauk SSSR, 224:1422–1444 (1975).
Kintya et al, "Rockogenin Glycosides", Khimiya Priorodnykh Soedinenii, 1L102–103 (1979).

Primary Examiner—Elbert L. Roberts
Attorney, Agent, or Firm—Ellen J. Buckles; Tom M. Moran; Alan M. Krubiner

[57] ABSTRACT

This invention discloses novel glycosides which are potent inhibitors of cholesterol absorption and therefore useful in treating hypercholesterolemia and atherosclerosis. Particularly useful in this respect is glycoside tigogenin cellobioside. The method of use for treatment of hypercholesterolemia and atherosclerosis, and the suitable pharmaceutical compositions are also disclosed.

14 Claims, 1 Drawing Figure

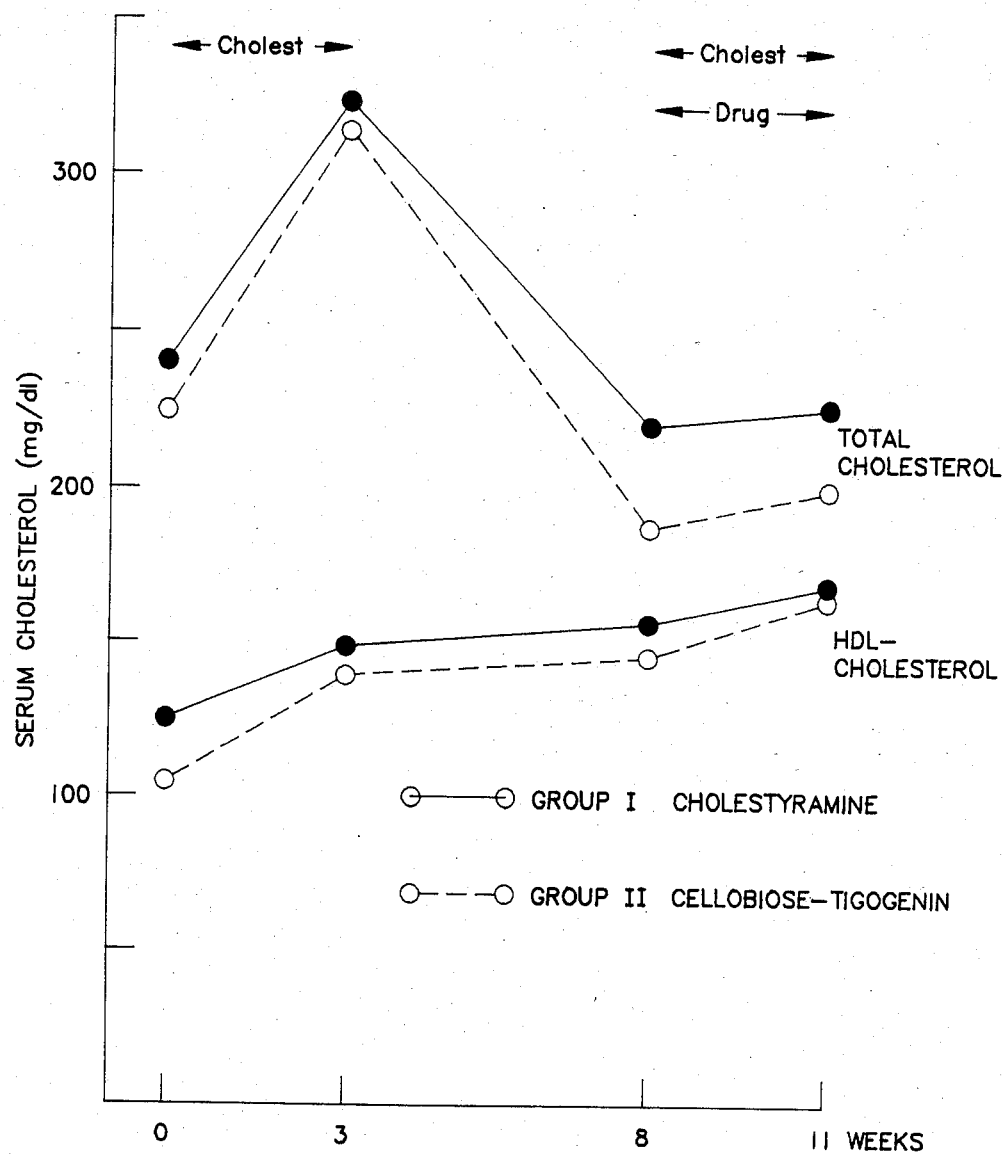

TIGOGENIN CELLOBIOSIDE FOR TREATING HYPERCHOLESTEROLEMIA AND ATHEROSCLEROSIS

This invention was made with government support under Grant No. 5 P51 RR00163 "Support for Regional Primate Research Center" awarded by the Department of Health and Human Services, Division of Research Resources. The government has certain rights in this invention.

BACKGROUND OF THE INVENTION

Field of the Invention

This is a continuation-in-part of the patent application Ser. No. 379,098, filled on May 17, 1982, pending. In the parent case, certain compounds were disclosed as being useful for treating a human or other warm-blooded animals to reduce the digestive absorption of cholesterol. At least one of those compounds, tigogenin cellobioside is novel and shows unexpectedly superior results in certain tests when compared to cholestyramine, a known inhibitor of the cholesterol absorption. Tigogenin cellobioside is also a better inhibitor of cholesterol absorption than certain other closely related, known glycosides.

This invention relates to the tigogenin cellobioside, tigogenin cellobioside heptaacetate and to the use of these compounds for treatment of hypercholesterolemia and atherosclerosis.

RELATED DISCLOSURES

French Pat. No. 2,425,859 and U.S. Pat. No. 4,260,603 describe the medicaments having activity as prostaglandin synthetase inhibitors which medicaments comprise certain sterol glycosides, a fatty acid ester thereof, or a spiroketal-steroid glucosides.

Hemolytic properties of tigogenin α-L-rhampyranoside and tigogenyl -maltoside are described in *J. Pharm. Sci.*, 67(11):1589 (1978).

SUMMARY

One aspect of this invention is a compound of formula

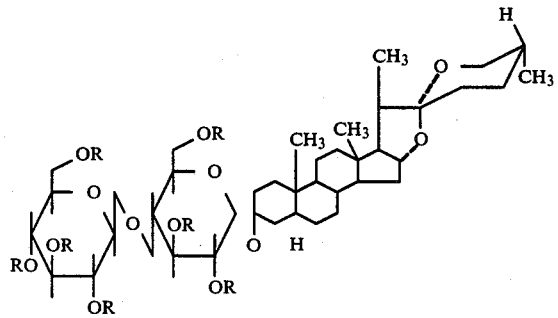

wherein R is hydrogen, namely tigogenin cellobioside, as an individual α- or β-anomer or a mixture thereof, which compound is useful in treatment of hypercholesterolemia and atherosclerosis.

Another aspect of this invention is a compound of the formula

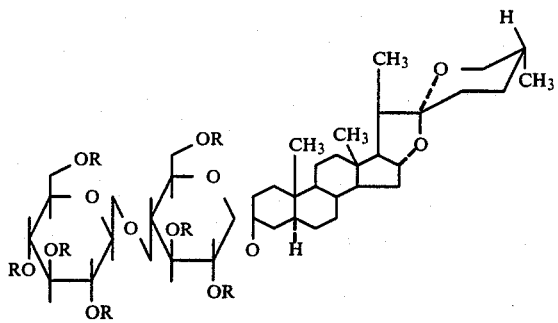

wherein R is $-C(O)CH_3$, namely tigogenin cellobioside heptaacetate, as an individual α- or β-anomer or a mixture thereof, which is an intermediate in the synthesis of tigogenin cellobioside.

Yet another aspect of this invention is the method of treating hypercholesterolemia and atherosclerosis by administering the compound of this invention to a subject in need of such treatment.

Still another aspect of this invention is a pharmaceutical composition comprising a therapeutically effective amount of a compound of this invention in admixture with suitable pharmaceutically acceptable excipient.

The last aspect of this invention is a process of making the compound of this invention, particularly the process of preparation of α- and β-anomers.

DETAILED DESCRIPTION OF THE INVENTION

Definitions

As used hereinafter:

"Tigogenin" means a compound of 5α,20α,22α, 25D-spirostan-3-ol, represented by the formula

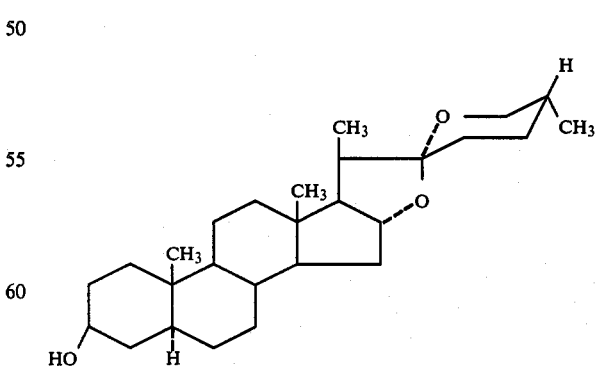

"Tigogenin cellobioside" means a non-separated mixture of α and β-anomers and an individual α- and β-anomer. It is depicted by the formula

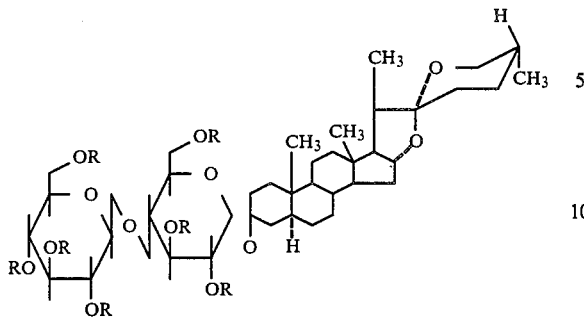

wherein R is hydrogen.

The wavy line illustrates the possibility that the steroid is attached to the cellobioside either above or below of the plane. "Tigogenin cellobioside heptaacetate" means a non-separated mixture of α- and β-anomers and an individual α- and β-anomer. It is depicted by the formula

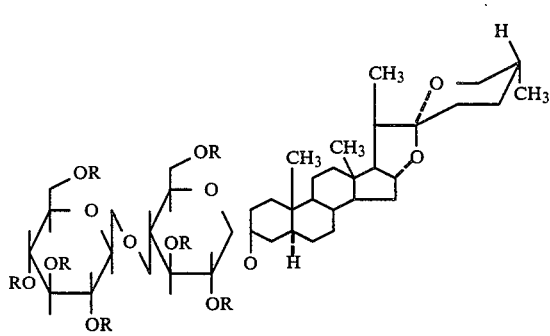

wherein R is —C(O)CH$_3$.

The wavy line illustrates the possibility that the steroid is attached to the cellobioside heptaacetate either above or below of the plane.

"α-Anomer" means the compound wherein the steroid is attached below the plane of the cellobioside.

"α-Tigogenin cellobioside" or "α-Tigogenin cellobioside heptaacetate" is depicted by the formula

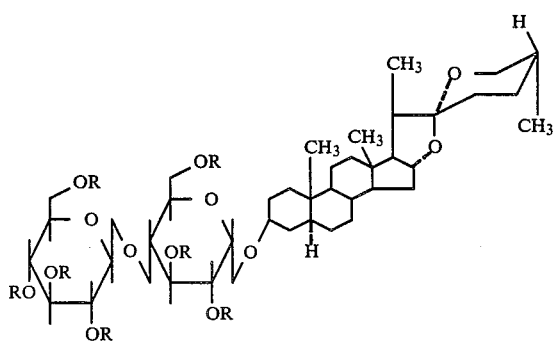

wherein R is hydrogen or —C(O)CH$_3$, respectively.

"β-Anomer" means the compound wherein the steroid is attached above the plane of the cellobioside.

"β-Tigogenin cellobioside" or "β-Tigogenin cellobioside heptaacetate" is depicted by the formula

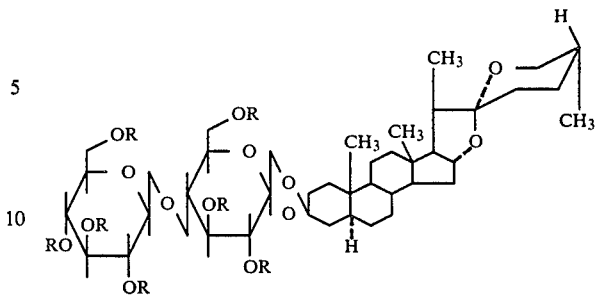

wherein R hydrogen or —C(O)CH$_3$, respectively.

"Mammals" means a class of warm-blooded vertebrates characterized by mammary glands, including but not limited to humans, laboratory or domestic animals such as dogs, cats, mice, rats or rabbits, and livestock.

"Treatment" covers any treatment of the disease in a mammal, particularly human, and includes:

(i) preventing the disease from occurring in a subject which may be predisposed to the disease but has not yet been diagnosed as having it;

(ii) inhibiting the disease, i.e. arresting the development of said disease; or (iii) relieving the disease, i.e. causing regression of the disease.

"Hypercholesterolemia", also known as hypercholesteremia or hypercholesterinemia, means the presence of an abnormally large amount of cholesterol in the cells and plasma of the circulating blood.

"Arteriosclerosis" as used herein means a degenerative arterial sclerosis marked by hardening and thickening of the vessel walls.

The types of arteriosclerosis generally recognized are atherosclerosis, Monckerberg's arteriosclerosis, hypertensive arteriosclerosis, arteriolosclerosis or senile arteriosclerosis.

"Atherosclerosis" as used herein means:

(i) deposition of lipid with proliferation of fibrous connective tissue cells in the inner walls of arteries;

(ii) modular sclerosis; arteriosclerosis characterized by irregularly distributed lipid deposits in the intima of large and medium-sized arteries. Such deposits are associated with fibrosis and calcification, and are almost always present in some degree in the middle-aged and elderly.

"Hypertensive arteriosclerosis" means progressive increase in muscle and elastic tissue of arterial walls resulting from hypertension. In longstanding hypertension elastic tissue forms numerous concentric layers in the intima and there is replacement of muscle collagen fibers and hyaline thickening of the intima of arterioles. Such changes can develop with increasing age even in the absence of hypertension and may then be referred to as senile arteriosclerosis.

"Monckeberg's arteriosclerosis" means (i) degeneration, (ii) sclerosis, or (iii) calcification.

Monckeberg's arteriosclerosis generally means arterial sclerosis involving the peripheral arteries, especially of the legs of older people, with deposition of calcium in the medial coat (pipe-stem arteries) but with little or no encroachment on the vessel lumen.

"Arteriolosclerosis" means arteriolar sclerosis. Arteriolosclerosis affects mainly the small vessels called arterioles. Arteriolosclerosis can be seen especially in patients with chronic hypertension.

PREFERRED EMBODIMENTS

This invention concerns a compound of the formula

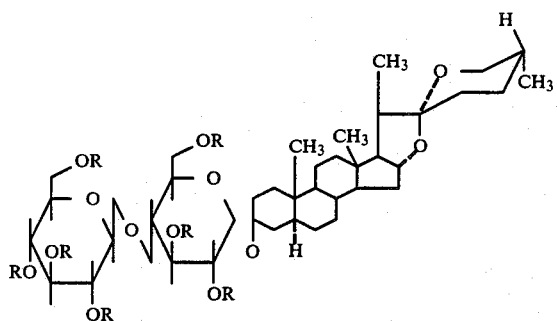

wherein R is either hydrogen or —C(O)CH₃, namely tigogenin cellobioside or tigogenin cellobioside heptaacetate, as an individual α-anomer, β-anomer or mixture thereof.

One preferred group of compounds are those wherein R is —C(O)CH₃, namely:
  α-tigogenin cellobioside heptaacetate;
  β-tigogenin cellobioside heptaacetate; or
  the mixture of α- or β-tigogenin cellobioside heptaacetate.

The second and most preferred group of compounds are those wherein R is hydrogen, namely:
  α-tigogenin cellobioside;
  β-tigogenin cellobioside; and
  the mixture of α- and β-tigogenin cellobioside.

PREPARATION PROCEDURES

Reaction Scheme 1 illustrates the preparation of tigogenin cellobioside (A). In the formula (A) and in the following text the term tigogenin cellobioside is meant to include the mixture of α- and β-anomers of tigogenin cellobioside or individual α-anomer, or β-anomer.

The R in formula (III) is —C(O)CH₃ and the R in formula (A) is hydrogen.

REACTION SCHEME 1

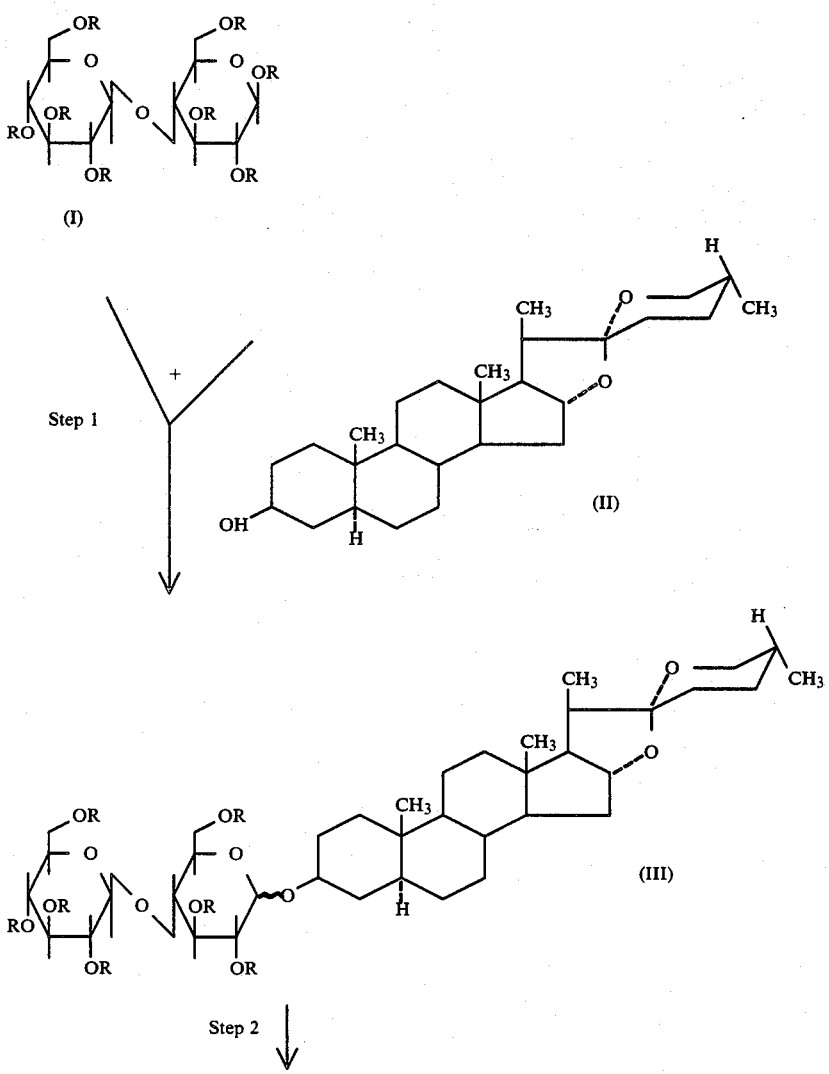

REACTION SCHEME 1
-continued

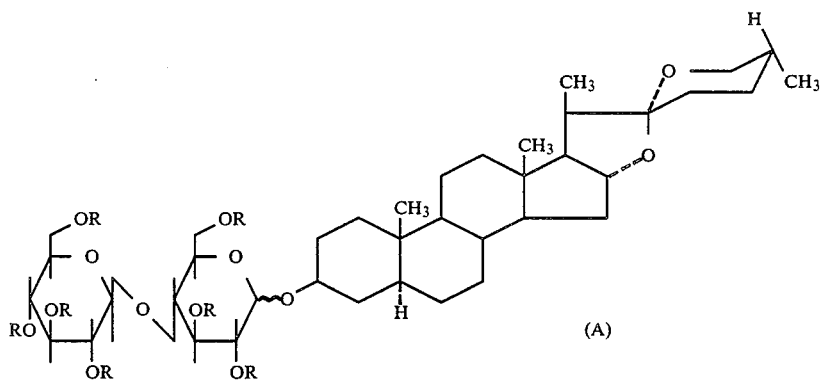

(A)

Reaction Scheme 1 illustrates processes of preparation of an individual α-anomer, or an individual β-anomer or a nonseparated mixture of both. All three processes use the same starting compounds, cellobiose octaacetate (I) and tigogenin (II), have the same intermediate, tigogenin cellobioside heptaacetate (III), and result in the same final compound (A).

Three procedures differ only in reaction conditions to give either individual α-anomer (Procedure 1) or individual β-anomer (Procedure 2) or the mixture of both (Procedure 3).

Procedures 1 and 2

Reaction conditions in Procedures 1 and 2 are essentially the same, except that a stereochemical modification is obtained using the different reaction solvent. *Tetrahedron Letters*, 28:1379 (1984) describe such solvent induced stereochemical modification. In this case, the use of acetonitrile gives the α-anomer. The use of the methylene chloride, on the other hand, gives β-anomer.

Step 1: Step 1 illustrates the conversion of tigogenin and cellobiose octaacetate to tigogenin cellobioside heptaacetate (III).

Both starting materials, cellobiose octaacetate and tigogenin, are commercially available from Aldrich and from Research Plus.

Cellobiose octaacetate (I) is reacted with tigogenin (II) in an organic solvent, preferably acetonitrile for preparation of α-anomer and methylene chloride for preparation of β-anomer, in approximate amounts of 65:200:5000; wt:wt:vol. Metal chloride, preferably stannic chloride, is added over a period of 1-5 minutes, preferably 2 minutes. The reaction mixture is warmed to a temperature between 50°-75° C., preferably to 65° C. or to the temperature when the mixture becomes homogeneous. That temperature is maintained for 10-60 minutes, preferably for 20 minutes, then cooled to 20°-40° C., preferably 30° C. The mixture is then submitted to purification procedures by methods known in the art to give, depending on the solvent which is used, the α- or β-tigogenin cellobioside heptaacetate (III).

Step 2: Step 2 illustrates the preparation of tigogenin cellobioside (A) by hydrolysis of compound (III).

Compound (III) is reacted with water and a mixture of organic solvents, preferably methylene chloride, triethylamine and methanol, in approximate amounts of 4:10:6:12:24; wt:v:v:v:v, at temperature of 20°-80°, preferably at reflux, for 2-10 hours, preferably for 6 hours. Then, the reaction mixture is stirred overnight at temperature of 15°-30° C., preferably at room temperature. The resulting material is evaporated, purified and separated by methods known in the art to give α- or β-tigogenin cellobioside (A), depending on which isomer of tigogenin cellobioside heptaacetate was used in the Step 2.

Procedure 3

Procedure 3 illustrates the preparation of the mixture of predominantly β-tigogenin cellobioside.

Step 1: Both tigogenin (I) and cellobiose octaacetate (II) are dissolved in an organic solvent, preferably in methylene chloride, in approximate amounts 4:80; w/v and 14:80; w/v, respectively. Metal salt, preferably stannic tetrachloride, is added to cellobiose octaacetate in an amount approximately equal to that of cellobiose octaacetate. Cellobiose solution is then added to tigogenin and reacted to 1-8 hours, preferably for 3 hours, at a temperature of 15°-30° C., preferably at room temperature. The mixture is washed with buffer, preferably with bicarbonate and the gas which develops during the reaction is removed. The mixture is submitted to purification and separation by techniques known in the art to yield the mixture of α- and β-tigogenin cellobioside heptaacetate (III).

Step 2: An organic solvents/water mixture, preferably triethylamine/methanol/methylene chloride/water and the solution of heptaacetate (III), obtained above, is reacted under constant stirring for 6-24 hours, preferably overnight at a temperature of 15°-30° C., preferably at room temperature. The solvent is removed and the residue is submitted to purification and separation by techniques known in the art. The purified mixture is dialyzed in a tilting dialyzer (described in Example 3) for 1-4 days, preferably for 3 days. The mixture is submitted to another purification procedure and extracted with an organic solvent, preferably heptane, in a soxhlet. The resulting residue is dried at 15° to 30° C., preferably at room temperature, for 1-4 days, preferably for 3 days, to yield a predominantly β-tigogenin cellobioside.

The mixture of α- and β-tigogenin cellobioside is obtained by mixing the proportional amounts of individual α- and β-anomers.

Isolation and purification of the compounds and intermediates described herein can be effected, if desired, by any suitable separation or purification procedure such as, for example, filtration, extraction, crystallization, column chromatography, thin-layer chromatography or thick-layer chromatography, or a combination of these procedures. Specific illustrations of suitable separation and isolation procedures can be had by reference to the examples hereinbelow. However, other equivalent separation or isolation procedures could, of course, also be used.

UTILITY AND ADMINISTRATION

Utility

This invention relates to certain glycosides which are potent inhibitors of cholesterol absorption and are therefore primarily useful for treatment of hypercholesterolemia. Since the hypercholesterolemia is closely related to the development of generalized cardiovascular, cerebral vascular or peripheral vascular disorders, secondarily these compounds prevent the development of atherosclerosis, particularly arteriosclerosis.

Cholesterol, which belongs to the body major plasma lipids, is highly soluble in fat but only slightly soluble in water. It is capable of forming esters with fatty acid and approximately 70% of the cholesterol present in plasma is in the form of cholesterol esters.

Cholesterol present in the body is either of endogenous or exogenous origin. Exogenous cholesterol is present in the diet and is absorbed slowly from the gastrointestinal tract into the intestinal lymph.

Endogenous cholesterol, in a rather large quantity, is formed in the cells of the body. Essentially, all the endogenous cholesterol that circulates in the lipoproteins of the plasma is formed by the liver, but all other cells of the body can and do form at least some cholesterol.

The major plasma lipids, including cholesterol, do not circulate free in the plasma, but are bound to proteins and transported as macromolecular complexes called lipoproteins.

The plasma lipoproteins can be separated into four major classes:
- chylomicrons;
- very low density lipoproteins (VLDL);
- low density lipoproteins (LDL); and
- high density lipoprotein (HDL).

Because of a varying ratio of lipid to protein, the densities of lipoproteins differ. The lipoproteins can be succefully separated by ultracentrifugation or by electrophoresis. The pathological hyperlipoproteinemias, which will be treated by the method of this invention, are classified on the basis of the pattern of lipoprotein abnormalities.

Chylomicrons: The largest lipoprotein particles, the chylomicrons, contain the most lipids and are thus of the least density. They have high molecular weights ($10^9$ to $10^{10}$) and consist of a core of nonpolar lipids (mostly triglycerides) surrounded by a coat of protein, phospholipid, and free cholesterol. Chylomicrons are secreted into the intestinal lymphatics by the intestinal mucosa following the absorption of a lipid-containing meal, and their triglycerides are eventually stored in adipose tissue.

Very-Low-Density-Lipoproteins: The (VLDL) are also triglyceride-rich. Their molecular weights are approximatey $5 \times 10^6$. These molecules are secreted by the liver, and their triglyceride is in part derived from dietary carbohydrates. Similar to the chylomicrons, VLDL triglycerides are mostly destined for storage in adipose tissue. On conventional electrophoresis, the VLDL migrate between the $\beta$- or low-density lipoproteins (LDL) and the $\alpha$- or high-density lipoproteins (HDL). In this electrophoretic scheme the VLDL are thus termed pre-$\beta$-lipoproteins. Because of the high triglyceride content of the chylomicrons and the VLDL, an increase in their concentration is accompanied by elevation in the concentration of the plasma triglycerides.

The fraction of VLDL which is rich in cholesterol is called $\beta$-VLDL, which term is derived from the mobility of these lipoproteins. Like chemically altered LDL, $\beta$-VLDL are transported by scavenger cells into the blood vessel wall thus resulting in formation of atheromatous foam cells, the initiator of atheromatous plaques.

Low-Density-Lipoproteins: The low density lipoproteins have the electrophoretic mobility of $\beta$-globulins and are therefore known as $\beta$-lipoproteins. These lipoproteins contain the major portion of the total plasma cholesterol. When LDL are present in increased concentration, plasma cholesterol concentration is increased, while the triglyceride concentration is relatively normal.

High-Density Lipoproteins: The high density lipoproteins are considerably smaller particles. These lipoproteins contain about 50% of protein and have the electrophoretic mobility of $\alpha$-globulins and are therefore termed $\alpha$-lipoproteins. Of their lipids, phospholipids predominate. Plasma levels of HDL are inversely correlated with risk of atherosclerosis.

Depending on the plasma lipoprotein pattern, it is possible to classify patients with three types of hyperlipemia abnormalities: hypercholesterolemia, combined hyperlipemia and hypertriglyceridemia.

Hypercholesterolemia, combined hyperlipemia and hypertriglyceridemia occur commonly and involve two classes of lipoproteins (VLDL and LDL) for which there is a positive correlation between plasma concentration and the incidence of atherosclerosis.

1. Hypercholesterolemia is characterized by the presence of the LDL $\beta$-lipoproteins. It may be genetic, sporadic, or secondary to various defined causes such as hypothyroidism, nephrotic syndrome, myeloma, and excess dietary cholesterol. If the hypercholesterolemia is of genetic origin, clinical manifestations of the disorder are usually evident before the age of 30. Until that age the risk of vascular disease seems to be greatly increased. The studies have shown that about 50% of individuals suffering from the genetic (familial) hypercholesterolemia have myocardial infarction before the age of 50.

2. Combined hyperlipemia is characterized by the presence of both LDL $\beta$-lipoproteins and VLDL pre-$\beta$-lipoproteins. In combined hyperlipemia, both plasma cholesterol and triglyceride concentrations are elevated. In a study of 500 survivors of myocardial infarction, one third had hyperlipemia. Familial combined hyperlipemia, often associated with a $\beta$- and pre-$\beta$-lipoprotein pattern, is the most common genetic cause and accounts for 30% of the hyperlipemic group.

3. Hypertriglyceridemia is characterized by the VLDL pre-$\beta$-lipoproteins. Hypertriglyceridemia is frequently encountered and is likewise associated with an increased risk of atherosclerosis. Patients with hypertriglyceridemia exhibit sensitivity to carbohydrates; that is, to a diet high in carbohydrates. Such diet results in elevated plasma concentrations of VLDL, the triglyceride of which is in part synthesized by the liver from carbohydrates. In this disorder, glucose tolerance is commonly abnormal, and diabetes mellitus is frequently associated with such an excess of VLDL.

For reference to the above, see Guyton, *Medical Biology*, 5th Ed., pp.926–927 (1976); *The Merck Index*, 13th Ed., pp.381–383 (1977) and Goodman and Gilman, *The Pharmacological Basis of Therapeutics*, 5th Ed., pp 744–747 (1975).

Inhibition of cholesterol absorption was studied in monkeys and rats using the commonly recognized screening tests.

The screening test which was used for determination of inhibition of cholesterol absorption in monkeys is described in *J. Clin. Invest.*, 67:156 (1981). An inhibitory activity of the compounds of this invention were compared to that of cholestyramine, known antilipoproteinemic drug, and were found to be five times or more potent. The same results as those obtained with 2% cholestyramine were obtained with the 0.4% tigogenin cellobioside. Since it is well known that the current treatment of hypercholesterolemia requires enormous daily dosages, this finding is of great importance. For example, the recommended adult dose of cholestyramine is 4 g three to four times daily which represents the total dose of 12–16 g of cholestyramine in admixture with 15–20 g of excipient. Thus, the total volume of the drug administered daily is between 27–36 g. On the other hand, the same effect has been obtained with the daily dose of only 0.8 g three to four times daily in a total dose of 2.4–3.2 g in admixture with 3–4 g of excipient, i.e. the total volume of the drug which is expected to be administered daily is between 5.4–7.2 g per day.

The percentage of cholesterol absorption in rat was studied by using the test described in *Am. J. Clin. Nutr.*, 30:2061 (1977). When compared to other synthetic glycosides such as structurally related diosgenin cellobioside, tigogenin glucoside, diosgenin glucoside or alfalfa saponins, compounds of the current invention had lower percentage of cholesterol absorption and thus were more effective in removing the cholesterol from the plasma.

Administration

Administration of tigogenin-cellobioside can be via any of the accepted modes of administration suitable for treatment of the hypercholesterolemia or atherosclerosis. These methods include oral routes, parenteral routes such as intravenous, subcutaneous, intradermal, or intramuscular and other systemic routes of administration such as, for example, by suppositories.

The amount of tigogenin cellobioside administered will, of course, be dependent on the subject being treated, on the severity of the affliction, on the manner of administration and on the judgment of the prescribing physician. However, an effective dosage is in the range of 7 to 115 mg/kg/day, preferably 28 to 57 mg/kg/day. For an average 70 kg human, this would amount to 0.5 to 8 g/day, preferably 2–4 g/day, most preferably 2.4–3.2 g/day.

For oral administration, which is preferred, a pharmaceutical composition takes the form of solutions, suspensions, tablets, pills, capsules, powders, sustained release formulations and the like.

Parenteral route of administration is the administration of drugs to a patient by injection under or through one or more layers of the skin or mucous membrane. Parenteral administration would preferably be reserved for crisis situations, wherein the subject is unable to swallow or administer the medication to himself.

Systemic administration via suppository is the administration of the drug in a solid but readily meltable cone or cylinder made of a tigogenin cellobioside and a suitable pharmaceutical excipient. Suppository must be suitable for insertion into a bodily passage or cavity, and is usually inserted into the rectum. This way of administration would be preferred in the patient with severe ingestion disturbance such as repeated vomiting.

Pharmaceutical Composition

Depending on the intended mode of administration, the pharmaceutical compositions may be in the form of solid, semi-solid or liquid dosage forms, such as, for example, tablets, pills, capsules, powders, liquids, suspensions, or the like, preferably in unit dosage forms suitable for single administration of precise dosages. The pharmaceutical compositions will include a conventional pharmaceutical carrier or excipient and, tigogenin cellobioside as an active ingredient. In addition, it may include other medicinal or pharmaceutical agents, carriers, adjuvants, etc.

A pharmaceutical composition may contain 0.1%–95% of tigogenin cellobioside, preferably 1%–70%. In any event, the composition or formulation to be administered will contain a quantity of tigogenin cellobioside in an amount effective to alleviate the signs of the subject being treated, e.i. hypercholesterolemia or atherosclerosis.

For solid pharmaceutical compositions, conventional non-toxic solid carriers include, for example, pharmaceutical grades of mannitol, lactose, starch, magnesium stearate, sodium saccharin, talcum, cellulose, glucose, sucrose, magnesium carbonate, and the like.

Liquid pharmaceutically administerable compositions can be prepared by dissolving or dispersing, or otherwise preparing tigogenin cellobioside, and mixing it optionally with a pharmaceutical adjuvant in a carrier, such as, for example, water, saline, aqueous dextrose, glycerol, ethanol, and the like, to thereby form a solution or suspension.

For parenteral administration, such as, for example, intravenous injections, the tigogenin cellobioside is dissolved in a vehicle. Vehicle may be, for example, aqueous vehicle, such as sodium chloride injection, Ringer's injection, dextrose injection and others, water miscible vehicle, such as ethyl alcohol, polyethylene glycol of the liquid series or propylene glycol, or nonaqueous vehicles such a corn oil, peanut oil or sesame oil. Vehicle will be buffered to the proper pH in order to stabilize a solution against chemical degradation and formed in such a way as to control isotonicity of injection. Other substances may also be added as antimicrobial or antioxidant agents.

A more recently devised approach for parenteral administration employs the implantation of a slow-release or sustained-release system, such that a constant level of dosage is maintained. See, e.g., U.S. Pat. No. 3,710,795.

For systemic administration via suppository, the tigogenin-cellobioside may be formulated as suppositories using as the carrier traditional binders and carriers such as, for example, polyalkylene glycols, or triglycerides. Such suppositories may be formed from mixtures containing tigogenin cellobioside in the range of 0.5%–10%; preferably 1–2%.

Methods of preparing various pharmaceutical compositions with a certain amount of active ingredient are known, or will be apparent, to those skilled in this art. For examples, see *Remington's Pharmaceutical Sciences*,

EXAMPLE 1

Preparation of α-Tigogenin Cellobioside

1. Preparation of α-Tigogenin Cellobioside Heptaacetate

A 12 l three neck round bottom flask fitted with a mechanical stirrer and a 500 ml dropping funnel was flushed with nitrogen and charged with 650 g (0.96 moles) of cellobiose octaacetate, 200 g (0.48 moles) of tigogenin, and 5 l of acetonitrile. A total of 250 g (0.96 moles) of stannic chloride was then added over two minutes through the dropping funnel. The reaction mixture was warmed on a steam bath, until it became homogeneous (65° C.). The 65° C. temperature was maintained for 20 min, then the mixture was cooled to 30° C. 4 liters of saturated aqueous sodium bicarbonate solution was added carefully and the mixture was vigorously stirred for 90 minutes. The layers were separated and the aqueous phase reextracted with 4 liters of methylene chloride. The combined organic phases were dried over magnesium sulphate and evaporated under reduced pressure to a gum. The gum was passed through a silica gel column (1.5 kg) eluted with 25% methylene chloride/hexane (v/v). The fraction which was obtained was evaporated under vacuum. The residue was crystallized from ethanol to give 120 g (24% of theory yield) of α-tigogenin cellobioside heptaacetate.

2. Preparation of α-Tigogenin Cellobioside

A mixture of 38.2 g of α-tigogenin cellobioside heptaacetate in 60 ml of methylene chloride, 240 ml of methanol, 120 ml of triethylamine and 100 ml of water was refluxed for 6 hours and then stirred overnight at room temperature. The reaction mixture was evaporated under reduced pressure to a thick paste which was washed with water and hexane and dried. The resulting material was chromatographed on a column of 3 kg of silica gel using 10% methanol/methylene chloride (v/v) to elute desired material. After evaporation of the fraction which contained α-tigogenin cellobioside, the residue was stirred in boiling isopropanol, cooled, and collected to give 13.9 g of α-tigogenin cellobioside.

NMR data for α- and β-tigogenin cellobioside are given in Table I which follows Example 3.

EXAMPLE 2

Preparation of β-Tigogenin Cellobioside

1. Preparation of β-Tigogenin Cellobioside Heptaacetate

A 12 liters three neck round bottom flask fitted with a mechanical stirrer and a 40 ml dropping funnel is flushed with nitrogen and charged with 650 g (0.96 moles) of cellobiose octaacetate, 200 g (0.48 moles) of tigogenin, and 500 ml of methylene chloride. A total of 250 g (0.96 moles) of stannic chloride is then added over two minutes through the dropping funnel. The reaction is warmed on a steam bath, and refluxed for 20 min, then cooled to 30° C. 4 liters of saturated aqueous sodium bicarbonate solution is added carefully and the mixture is vigorously stirred for 90 minutes. The layers are separated and the aqueous phase reextracted with 4 liters of methylene chloride. The combined organic phases are dried over magnesium sulphate and evaporated under reduced pressure to a gum. The gum is passed through a silica gel column (1.5 kg) eluting with 25% methylene chloride/hexane (v/v). The fraction containing β-tigogenin cellobioside is evaporated under vacuum. The residue is crystallized from ethanol to give β-tigogenin cellobioside heptaacetate.

2. Preparation of β-Tigogenin Cellobioside

A mixture of 38.2 of β-tigogenin cellobioside heptaacetate in 60 ml of methylene chloride, 240 ml of methanol, 120 ml of triethylamine and 100 ml of water, is refluxed for 6 hours, then stirred overnight at room temperature. The reaction mixture is evaporated under reduced pressure to a thick paste which is washed with water and hexane and dried. The resulting material is chromatographed on a silica gel column of 3 kg of silica gel using 10% methanol/methylene chloride (v/v) to elute desired material. After evaporation of the appropriate fractions, the residue is stirred in boiling isopropanol, cooled, and evaporated to give β-tigogenin cellobioside.

EXAMPLE 3

Preparation of β-Tigogenin Cellobioside

General Information and Procedures

Tigogenin was obtained from Research Plus.
Cellobiose octaacetate was obtained from Aldrich.
Tilting dialyzer: A tilting dialyzer was built using a large container provided with a siphon in such a way that the water level was continuously rising and falling. The dialysis bags were tied to a vertical metal rod midway between the upper and lower water levels. The tilting bags moved the powdered material and increased its contact with water.

Experimental Procedure

Tigogenin: 41.9 g of tigogenin (100 mmoles) was dissolved in 800 ml of water-free methylene chloride.

Water-free methylene chloride: Water-free methylene chloride was prepared by adding the $MgCl_2$ to a commercially obtained methylene chloride. The solution was stirred for 30 min and filtered.

Cellobiose octaacetate: 135 g of cellobiose octaacetate (200 mmoles) is dissolved in 800 ml of water-free methylene chloride and 25 ml of stannic tetrachloride (200 mmoles) was added. The mixture was stirred for 10 minutes.

The cellobiose octaacetate mixture, obtained above, was introduced into a separatory funnel and added dropwise to a solution of tigogenin, obtained above, at an approximate rate of 150 ml/min. The mixture was stirred for 3 hours. The resulting solution was poured into 4 liter separatory funnel containing 500 ml of saturated bicarbonate solution saturated with methylene chloride. 500 ml of water saturated with methylene chloride was added and the gas was allowed to escape. The solution was mixed by inversion and separated into an organic and water phases. Lower phases were transferred to a separatory funnel, washed twice with water saturated with methylene chloride and, after separation, the upper phase was aspirated and discarded. The remaining phase was washed twice with 250 ml of water, separated, and again the upper phase was discarded. The lower phase was washed twice with water, separated and again the lower phases were collected and evaporated to 100–200 ml at approximately 50° C. under vigorous stirring and nitrogen atmosphere to give predominantly β-tigogenin cellobioside heptaacetate.

1400 ml of a mixture containing triethylenamine/methanol/water (1:2:1) was added slowly and under constant stirring to the solution of the above tigogenin cellobioside heptaacetate. The mixture was stirred overnight. Methylene chloride was removed at 30° C. under vacuum. Three liters of water was added and the mixture was left in the refrigerator for 1 to 2 hours. Afterwards, the mixture was centrifuged at 4000 RPM for 20 min, precipitate dried at room temperature, crushed, dissolved in small amount of methanol and water, and dialized for 3 days in tilting dialyzer against running tap water. The resulting mixture was filtered, dried at room temperature, crushed into fine powder and extracted in Soxhlet (jacketed at 40°) with heptane for 3 days. β-tigogenin cellobioside which remained in the thimble was removed and dried at room temperature for 2 to 3 days to evaporate heptane. This procedure yielded 30 to 40% of β-tigogenin celobioside.

The 'H NMR spectra of 1'α- and 1'β-tigogenin cellobioside were measured on the Bruker WM300 Fourier transform NMR spectrometer in $d_6$DMSO solution with reference to internal tetramethylsilane.

TABLE I

300 MHz 'H NMR Data in $d_6$DMSO

Chemical Shifts in ppm
Cellobioside

| Assignments | α-tigogenin | β-togenin | No. of Protons |
|---|---|---|---|
| 16α | 4.28 m | 4.25 m | 1 |
| 18 | 0.72 s | 0.72 s | 3 |
| 19 | 0.78 s | 0.78 s | 3 |
| 21 | 0.89 d, d,J=6.8 Hz | 0.89 d,J=6.8 Hz | 3 |
| 26 | 0.74 d,J=6.3 Hz | 0.73 d, J=6.3 Hz | 3 |
| 1' | 4.78 d,J=3.5 Hz | 4.29 d,J=7.9 Hz | 1 |
| 1" | 4.23 d,J=7.6 Hz | 4.23 d,J=7.6 Hz | 1 |

J = coupling constant
s = singlet
d = doublet
m = multiplet

EXAMPLE 4

Effect of Tigogenin Cellobioside on Plasma Cholesterol

This example illustrates the effect of tigogenin cellobioside on plasma cholesterol in monkeys *Macaca fascicularis*. The procedure is described in *J. Clin. Invest.*, 67:156 (1981).

Experimental procedure

Experimental Regimen

The animals were divided into groups I and II. Group I was treated with 2% cholestyramine, Group II was treated with 0.4% tigogenin cellobioside. Each group was divided into two subgroups. Animals in the first subgroup served as cholesterol controls, i.e. they received no drug treatment but were fed with a cholesterol diet. Animals in the second group received a drug treatment and were also fed with a cholesterol diet.

Subgroup 1: Before the beginning of the experimental regimen, the control blood was obtained from all animals in both groups and a total cholesterol and a high density lipoprotein cholesterol were determined. Then the animals were fed the cholesterol diet. After three weeks on the diet without treatment, the blood from treated monkeys was collected and a total cholesterol and a high density lipoprotein cholesterol were determined.

Subgroup 2: Before the beginning of the regimen of subgroup 2, the animals from subgroup 1 were fed cholesterol-free semipurified diet for five weeks. After five weeks on the cholesterol-free diet, the control blood was again obtained from all animals and a total cholesterol and a high density lipoprotein cholesterol were determined. Then, the animals were put on a cholesterol diet combined with drug treatment. After three weeks of the cholesterol diet and of the appropriate treatment, the blood from all monkeys was collected and a total cholesterol and a high density lipoprotein cholesterol were determined.

Animals and diet

Twelve adult female cynomolgus (*Macaca fascicularis*) were fed for 3 weeks the cholesterol-free semipurified diet (SPD) of the following content:

| Ingredient | g/100 g of diet |
|---|---|
| casein | 18 |
| sugar | 30 |
| honey | 10 |
| Alphacel | 12 |
| butter | 3 |
| coconut oil | 8.5 |
| safflower oil | 2.5 |
| vitamins (OWP) | 2 |
| salts (Hegsted IV) | 4 |
| vitamin D-3 (2,000 IU/ml) | 0.2 ml |
| banana (wet weight) | 10 |
| proteins (% calories) | 20.6 |
| fat (% of calories) | 33.5 |
| carbohydrate (% of calories) | 45.9 |

This diet can optionally contain 0.118 g/100 g of diet or 0.35 mg/kCal of cholesterol.

The experimental protocol is outlined and the results are summarized in Table A.

Results (summarized in Table A)

The monkeys were assigned to two groups (I and II) according to their serum cholesterol response; they were stratified and assigned randomly, thus resulting in groups with similar elevations of cholesterolemia.

Control 1, Sample 1

Control venous blood was obtained for analysis and the mean values of the serum cholesterol were determined to be 240 mg/dl for Group I and 228 mg/ml for Group II.

Then, the monkeys were offered semipurified diet containing 0.1% cholesterol for 3 weeks. At the end of this period, blood sample 2 was obtained.

Cholesterol Diet, Sample 2

After three weeks on the cholesterol diet, the mean value of cholesterol was 324 mg/dl in Group I and 316 mg/dl in Group II. The level of cholesterol was significantly higher in samples 2, with degree of significance ≦0.01.

The monkeys were again given semipurified diet without cholesterol for 5 weeks and bled at the end of this period.

Control 2, Sample 3

After five weeks on the cholesterol-free diet, the level of cholesterol in both groups decreased to 221 mg/dl in Group I and to 189 mg/dl in Group II.

The animals were then given semipurified diet with 0.1% cholesterol and either 2% cholestyramine (Group I) or 0.4% cellobiose tigogenin (Group II) for 3 weeks. At the end of this period, sample 4 was obtained.

Cholesterol Diet and Drug Treatment, Sample 4

After three weeks on the cholesterol diet combined with the drug treatment, the values of cholesterol in Group I was 226 mg/dl and 202 mg/dl in Group II.

Results shown in Table A and FIG. 1 demonstrate that both drugs prevented the expected rise in serum cholesterol. There were small, nonsignificant elevations in high-density lipoprotein-cholesterol associated with drug intake. See Samples 1, 2, 3 and 4 in HDL cholesterol section of the Table A. Although the changes in the triglyceride levels would be a natural response to the ingestion of a high-cholesterol diet, no changes were found. This indicates that both drugs prevented the increase in low-density lipoprotein cholesterol.

Group III has two subgroups with 12 animals in each. An inhibition of the cholesterol absorption in rats treated with tigogenin cellobioside was compared to the inhibition of the cholesterol absorption in nontreated controls.

Similarly to Group I, wherein treatment with tigogenin cellobioside inhibited absorption of cholesterol by 47% (No=6), in Group III the treatment with tigogenin cellobioside inhibited absorption of cholesterol by 41.5% (No=12). And, the absorption of cholesterol in experimental rats in Group I was only 53% and the absorption of cholesterol in Group III was only 58.5% of the absorption of cholesterol in control group.

TABLE A

| | Serum cholesterol (mg/dl; mean ± SE)[a] | | | | | | | |
|---|---|---|---|---|---|---|---|---|
| | Total Cholesterol | | | | HDL Cholesterol | | | |
| Period Sample | Control 1 1 | Cholesterol diet 2 | Control 2 3 | Cholesterol diet + drug 4 | Control 1 1 | Cholesterol diet 2 | Control 2 3 | Cholesterol diet + drug 4 |
| GROUP I N = 6 Drug: 2% cholestyramine paired t test | 240 ± 19 | 324 ± 24 | 221 ± 19 | 226 ± 16 | 126 ± 12 | 148 ± 17 | 155 ± 9 | 166 ± 8 |
| P: vs column 2 | 0.01 | — | 0.001 | 0.01 | NS | — | NS | NS |
| vs column 1 | — | 0.01 | NS | NS | — | NS | 0.02 | 0.05 |
| vs column 3 | | | | NS | | | | NS |
| GROUP II N = 6 Drug: 0.4% cellobiosetigogenin paired t test | 228 ± 19 | 316 ± 21 | 189 ± 10 | 202 ± 8 | 104 ± 12 | 139 ± 14 | 148 ± 10 | 163 ± 7 |
| p: vs column 2 | 0.01 | — | 0.01 | 0.01 | 0.05 | — | NS | NS |
| vs column 1 | — | 0.01 | 0.05 | 0.05 | — | 0.05 | 0.05 | 0.01 |
| vs column 3 | | | | NS | | | | NS |

[a]Abbreviations:
HDL-cholesterol, high density lipoprotein cholesterol;
N, number of animals;
NS, not significant.

EXAMPLE 5

Effect of Synthetic Glycosides on Intestinal Absorption of Cholesterol in Rats

This example illustrates the effect of synthetic glycosides on intestinal absorption of cholesterol in rats. The method used for this experiment is described in detail by Malinow et al., Am. J. Clin. Nutr., 30:2061 (1977).

Experimental Protocol 2-mg bolus of 4[$^{14}$C]cholesterol was given intragastrically to rats. Feces were collected for 72 hours, and the fecal excretion of labeled neutral steroids was determined.

Rats were divided into three groups I–III.

In Groups I and II the animals were divided into subgroups of 6 rats. The first subgroup served as control and never received any treatment. The second and third subgroups were treated with either a compound of this invention or with one of the others closely related compounds. Thus, in Groups I and II, the rats were treated with tigogenin cellobioside, diosgenin cellobioside, tigogenin glucoside and diosgenin glucoside.

Results summarized in Table B confirm that the tigogenin cellobioside decreased an intestinal absorption of cholesterol more markedly than structurally similar compounds diosgenin cellobioside, tigogening glucoside and diosgenin glucoside. Tigogenin cellobioside was significantly more effective than closest related diosgenin cellobioside (see Group I, subgroups 2 and 3). When compared to control group, tigogenin cellobioside decreased the cholesterol absorption by almost 50% (with significance of ≦0.001). The tigogenin cellobioside was also more effective than tigogenin glucoside and diosgenin glucoside (see Group II, subgroups 2 and 3, and compare Group I and II).

TABLE B

Effects of Synthetic Saponins of Cholesterol Absorption in Rats

| Group | Treatment | Number of animals | Dose (mg) | Cholesterol absorption (% I.D.) | P (Student's t test vs control) | Relative Absorption |
|---|---|---|---|---|---|---|
| I | none | 6 | 0 | 74.8 ± 1.6 | | 100 |
| | C-T | 6 | 14 | 39.6 ± 1.8 | <0.001 | 53 |
| | C-D | 6 | 14 | 53.7 ± 1.3 | <0.001 | 72 |
| II | none | 6 | 0 | 74.6 ± 2.3 | | 100 |
| | G-T | 6 | 14 | 46.2 ± 1.8 | <0.001 | 62 |
| | G-D | 6 | 14 | 52.6 ± 3.7 | <0.001 | 71 |
| III | none | 12 | 0 | 75.2 ± 1.8 | | 100 |
| | C-T | 12 | 14 | 43.6 ± 1.6 | <0.001 | 58.5 |

Mean ± SE.
Abbreviations:
C-D, cellobiose diosgenin;
C-T, cellobiose tigogenin;
G-D, glucose diosgenin;
G-T, glucose tigogenin.

I claim:
1. A compound of the formula

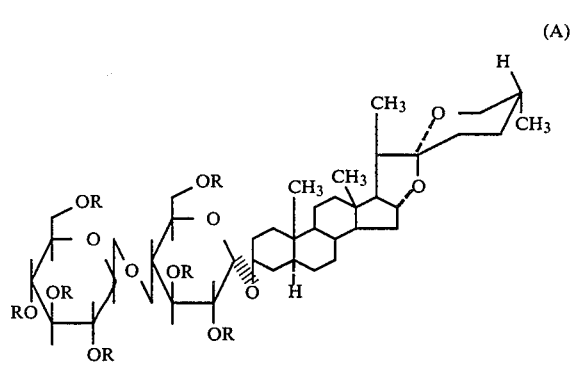

(A)

wherein R is hydrogen; namely, tigogenin cellobioside.

2. The compound of claim 1 wherein the compound is α-anomer, namely α-tigogenin cellobioside.

3. The compound of claim 1 wherein the compound is the β-anomer, namely β-tigogenin cellobioside.

4. A method of treating hypercholesterolemia and atherosclerosis in a mammal which method comprises administering to a mammal in need of such treatment a therapeutically effective amount of compound of formula

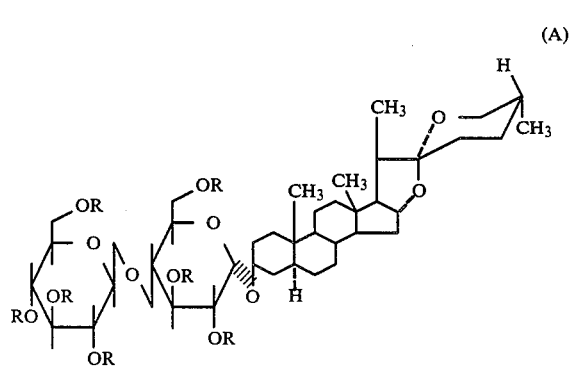

(A)

wherein R is hydrogen, namely tigogenin cellobioside.

5. The method of claim 4 wherein the compound is α-tigogenin cellobioside.

6. The method of claim 4 wherein the compound is β-tigogenin cellobioside.

7. A pharmaceutical composition useful for treatment of hypercholesterolemia and atherosclerosis in mammals which composition comprises a pharmaceutically effective amount of a compound of formula

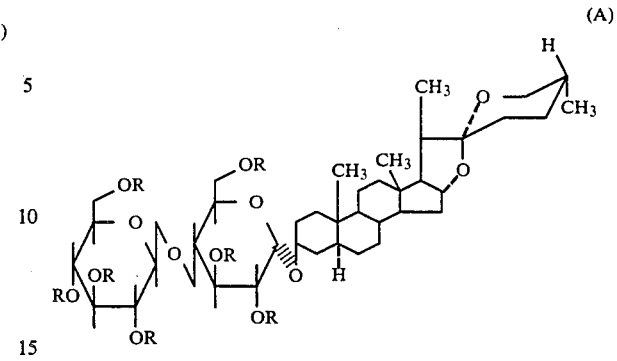

(A)

namely, tigogenin cellobioside in admixture with a pharmaceutically acceptable excipient.

8. The composition of claim 7 wherein the compound is the α-anomer, namely α-tigogenin cellobioside.

9. The composition of claim 7 wherein the compound is the β-anomer, namely β-tigogenin cellobioside.

10. A compound of the formula

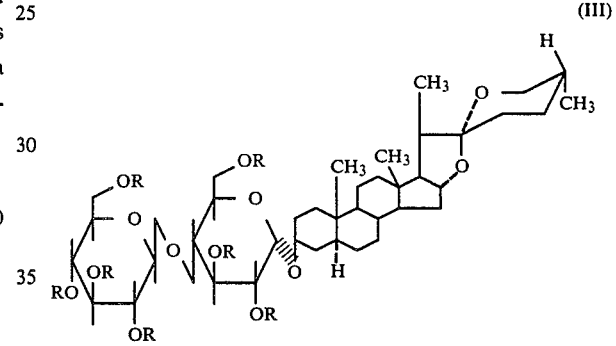

(III)

wherein R is —C(O)CH₃, namely tigogenin cellobioside heptaacetate.

11. The compound of claim 10 wherein the compound is an α-anomer, namely α-tigogenin cellobioside heptaacetate.

12. The compound of claim 10 wherein the compound is a β-anomer, namely β-tigogenin cellobioside heptaacetate.

13. A method of treating hypercholesterolemia and atherosclerosis in mammals which method comprises administering to a mammal in need of such treatment a therapeutically effective amount of compound of claim 10.

14. A pharmaceutical composition useful for treatment of hypercholesteremia and atherosclerosis in mammals which composition comprises a pharmaceutically effective amount of a compound of claim 10 in admixture with a pharmaceutically acceptable excipient.

* * * * *